(12) United States Patent
Stein et al.

(10) Patent No.: US 6,582,679 B2
(45) Date of Patent: Jun. 24, 2003

(54) HAIR WAX PRODUCTS CONTAINING WAXES, NON-VOLATILE OILS AND VOLATILE HYDROPHOBIC MATERIALS

(75) Inventors: Bernd Stein, Hoesbach (DE); Michael Franzke, Rossdorf (DE); Sabine Baecker, Ruesselsheim (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/968,102

(22) Filed: Oct. 1, 2001

(65) Prior Publication Data

US 2002/0122811 A1 Sep. 5, 2002

(51) Int. Cl.⁷ .............................. A61K 7/00; A61K 7/06; A61K 7/075; A61K 7/08; A61K 9/00
(52) U.S. Cl. ..................... 424/47; 424/70.1; 424/70.31; 424/400; 424/401; 424/DIG. 1; 514/945
(58) Field of Search ................................. 424/401, 400, 424/70.1, 47, 70.31, DIG. 1; 514/945

(56) References Cited

U.S. PATENT DOCUMENTS

| | | |
|---|---|---|
| 4,001,391 A | 1/1977 | Feinstone et al. |
| 5,252,331 A | 10/1993 | Curtis et al. |
| 5,306,488 A * | 4/1994 | Vanlerberghe et al. ... 424/70.31 |
| 5,505,937 A | 4/1996 | Castrogiovanni et al. |
| 6,033,650 A | 3/2000 | Calello et al. |
| 6,066,316 A * | 5/2000 | Shiojima et al. ............ 424/401 |

FOREIGN PATENT DOCUMENTS

| | | |
|---|---|---|
| EP | 0 106 762 A1 | 4/1984 |
| EP | 0 779 351 A1 | 6/1997 |
| EP | 0 795 317 A2 | 9/1997 |
| EP | 0 868 898 A1 | 10/1998 |
| EP | 0 997 139 A1 | 5/2000 |
| WO | 97/16157 | 5/1997 |
| WO | 98/50002 | 11/1998 |

* cited by examiner

Primary Examiner—Jose' G. Dees
Assistant Examiner—Marina Lamm
(74) Attorney, Agent, or Firm—Michael J. Striker

(57) ABSTRACT

The wax product for treating or setting up a hairstyle or hairdo includes a composition containing at least one wax or wax-like substance, at least one non-volatile liquid hydrophobic oil and at least one volatile or easily volatilized hydrophobic substance that is a liquid or gas at room temperature. Because of the presence of the volatile substance in the composition a soft wax easily worked in the hair is obtained when the composition is applied to the hair. This soft wax hardens on the hair when the volatile ingredients evaporate. When the composition includes a propellant gas a wax with a larger surface area (wax snow) is produced, which is likewise easily worked into the hair and very effectively fixes or sets the hair.

19 Claims, No Drawings

HAIR WAX PRODUCTS CONTAINING WAXES, NON-VOLATILE OILS AND VOLATILE HYDROPHOBIC MATERIALS

BACKGROUND OF THE INVENTION

1. Field of the Invention

The subject matter of the present invention is a wax product for treatment of or setting up a human hairstyle. The wax product of the present invention contains a composition comprising a wax or wax-like substance, a non-volatile hydrophobic oil that is a liquid at room temperature and an easily volatilized hydrophobic substance that is a liquid or gaseous material at room temperature.

2. Description of Related Art

Styling wax compositions are known products for hair treatment. They particularly find application in putting short to medium length hair in a fashionable hairstyle and impart hold and luster as well as stabilize, condition and fix the hairstyle. They provide the hairstyle with shape and luster. Conventional hair wax is usually provided in cups or other vessels and its action is based on the following principle: Product is removed with the fingers. The wax is distributed on the surface of the hand and then melted or at least considerably softened by the heat of the hand. It is possible to work the otherwise too hard wax into the hair because of this softening or melting. The wax is worked into the hair in a softened or more or less liquid state. Then it cools and again reaches its original consistency. It hardens and the hairdo obtained has stability and hold and frequently a slightly wet look. The limits of the product performance of conventional styling wax products are established by this action principle. So that the wax may be worked into the hair to a sufficient extent, it must not be too hard to be removed with the hand, and the melting or softening point must be near the body temperature. On the other hand, only moderate product performance is attained regarding hair conditioning and hold and volume of the hairdo. In addition, the load on the hair is comparatively high. Of course an improved fixing and improved hold may be obtained with a harder wax composition, however the harder the wax, the harder is the product mass and the more difficult it is to process it and work it in the hair.

SUMMARY OF THE INVENTION

It is an object of the present invention to provide a hair wax product, which improves the hold of the hairstyle and conditions the hair. At the same time the product mass should be easily and satisfactorily processed and worked in the hair.

It is also an object of the present invention to provide a hair wax product that is not removed from its cup or other container with the fingers, which can lead to impurities in the residual product remaining in the cup, and, which avoids contamination of the product mass.

It has now been found that these requirements were fulfilled by a wax product for treatment or preparation of a hairdo of a person, which contains a composition comprising a wax or wax-like substance, non-volatile hydrophobic oil that is a liquid at room temperature and an easily volatilized hydrophobic substance that is a gas or liquid at room temperature. The wax product according to the invention can either be a cup product with a waxy or wax-like consistency or it can be a non-aerosol spray product from which a spray or foam is generated from the wax-containing composition. This latter composition is preferably a liquid and contains a comparatively high proportion of especially easily volatilized substances, such as pentane. The hair wax product according to the invention can also be an aerosol spray product. The wax material is preferably dissolved or suspended in a liquid hydrophobic propellant gas in the case of the aerosol spray product.

By using easily volatilized substances, such as pentane, isododecane or others, a soft easily processed and easily worked-into-the-hair wax can be obtained, which hardens on the hair by evaporation of the easily volatilized ingredient. The hair wax product according to the invention provides improved conditioning, more volume and lesser load on the treated hair in comparison to the conventional hair wax. Tough wax-like compositions (cup or pan waxes) to sprayable liquid compositions (spray waxes) are obtained by variation of the type and amount of the easily volatilized substances in the composition according to the invention. Waxes having especially large surface areas (wax snows) can be made by using gaseous substances (propellant gases, such as propane, butane, and the like). These wax snows are easily processed and gently worked into the hair in spite of the stronger fixing effect.

The hair wax product according to the invention for treatment or preparation of a human hairstyle comprises a waxy-like composition comprising (A) at least one wax or wax-like substance;
(B) at least one non-volatile hydrophobic oil that is liquid at room temperature; and
(C) at least one easily volatilized, hydrophobic substance that is liquid or gaseous at room temperature.

The term "room temperature", as usual, means a temperature of 20° C., or about 20° C.

The "wax-like, waxy or wax-form substances" are those which fall under the definition of "wax" in Ullmanns' Encyclopedia for Industrial Chemistry, 4th Edition, Volume 24, page 3. According to this definition these substances are plastic at 20° C., solid to brittle, gross to fine crystalline, transparent to opaque, but not glassy, melting over 40° C. without decomposition. They have a comparatively low viscosity above their melting point, have a consistency and solubility that is comparatively temperature dependent and are polishable with a gentle pressure.

In the hair wax product according to the invention that is provided in a cup or pan the wax-like or waxy composition has a needle penetration number (measurement unit, 0.1 mm, test weight 100 g, test duration 5 c, test temperature of 25° C., according to DIN 51 579) of greater than or equal to 10, preferably 20. The wax or wax-like substances (A) are preferably contained in the composition in an amount of from 20 to 60 percent by weight, especially preferably from 30 to 50 percent by weight. The liquid hydrophobic oil (B) is preferably contained in an amount of from 10 to 35 percent by weight, especially preferably from 15 to 30 percent by weight. The easily volatilized, hydrophobic substance (C) that is liquid or gaseous at room temperature is preferably contained in an amount of from 10 to 35 percent by weight, especially preferably from 15 to 30 percent by weight. A portion of the non-volatile oils is replaced by the easily-volatilized hydrophobic materials in comparison to the conventional hair wax products. The ratio of non-volatile oils (B) to easily-volatilized substances (C) amounts preferably to from 1:2 to 2:1, especially preferably from 1:1 to 1:1.5. The term "easily-volatilized substance" means a substance, which evaporates when applied to the hair. The boiling points of these substances are typically around 250° C. and thereunder.

The easily-volatilized hydrocarbon substance (C) for the hair wax product preferably is liquid at room temperature and has a boiling point in a range from 30 to 250° C., especially preferably from 60 to 220° C. Liquid hydrocarbons, liquid cyclic or linear silicones (dimethylpolysiloxanes), or mixtures of the foregoing substances, are suitable, for example. Suitable hydrocarbons include paraffins or isoparaffins with 5 to 14 carbon atoms, especially preferably with 8 to 12 carbon atoms, especially dodecanes or isododecane. Suitable liquid, easily volatilized silicones include cyclic dimethylsiloxanes with 3 to 8, preferably 4 to 6, silicon atoms, especially cyclotetradimethylsiloxane, cyclopentadimethylsiloxane or cyclohexadimethylsiloxanes. Dimethylsiloxane/methylalkylsiloxane cyclocopolymers, for example, silicone FZ 3109 of Union Carbide, which is a dimethylsiloxane/methyloctylsiloxane cyclocopolymer. Suitable volatile linear silicones have 2 to 9 silicon atoms. Alkyltrisiloxanes, such as hexylheptamethyltrisiloxane or octylheptamethyltrisiloxane, are especially suitable.

A non-aerosol spray wax product is also part of the subject matter according to the invention. The non-aerosol spray wax article consists of a container with a mechanical pumping device and a spray head or foam head, which contains a sprayable or foamable composition that is a liquid at room temperature. The sprayable or foamable composition comprises (A) at least one wax or wax-like substance;
(B) at least one non-volatile, hydrophobic oil, which is liquid at room temperature; and
(C) at least one easily-volatilized, hydrophobic substance that is liquid or gaseous at room temperature.

When the hair wax product according to the invention is a non-aerosol spray wax product, the wax-containing composition preferably has a liquid, sprayable or foamable consistency at room temperature of 20° C. The waxy or wax-like substance (A) is preferably contained in the non-aerosol spray wax product in an amount of from 10 to 30 percent by weight, especially preferably from 15 to 25 percent by weight. The liquid hydrophobic oil (B) is preferably present in an amount of from 10 to 30 percent by weight, especially preferably from 15 to 25 percent by weight. The easily-volatilized hydrophobic material (C) is present in an amount of preferably from 25 to 80 percent by weight, especially preferably 30 to 70 percent by weight. A part of the non-volatile oils are replaced by easily volatilized hydrophobic substances in comparison to the conventional hair wax products.

The easily volatilized hydrophobic substance (C) is preferably liquid at room temperature and has a boiling point in the range of 30 to 100° C., preferably 35 to 70° C., when it is used in the non-aerosol spray wax product. Liquid hydrocarbons, liquid cyclic or linear silicones (dimethylpolysiloxanes), or mixtures of the foregoing materials, are suitable. Linear or branched alkanes with 5 to 7 carbon atoms are especially suitable hydrocarbons. Pentane is particularly preferred. Hexamethyldisiloxane is especially preferred as a liquid easily-volatilized silicone.

The container for the non-aerosol spray wax product according to the invention can be made from any known material suitable for non-aerosol spray or foam products, in so far as the material is sufficiently pressure-resistant to slight increases in pressure due to the easily-volatilized hydrophobic material (C) and provides a sufficient barrier to diffusion of the ingredients of the composition contained in the container. Metals, such as aluminum or tin plate, or plastic are suitable materials. Transparent or at least translucent materials are preferred so that the product consistency and/or the amount of product left in the container is visible from the outside of the container. The product container is preferably made from glass or polyethylene terephthalate (PET).

Commercially available pumps, spray heads and foam heads can be used with the container for the non-aerosol spray wax product according to the invention. There are however special requirements for the materials from which the spray pump is made, when pentane is present in the composition contained in the container. The plastic cylinders for the conventional spray pumps for pumped hair sprays, which are made, for example, from polypropylene, can swell when in contact with organic solvents, such as pentane. These standard pumps would be damaged in a short time in operation when used for a composition containing pentane. A spray pump, which is made from a material that is resistant to swelling in the presence of pentane, is thus preferable. This sort of material is, for example, polyoxymethylene (POM). One spray pump suitable according to the invention is, for example, the Seaquist-Perfect PZ1/100 HVT fine spray pump.

An aeration opening is not required in contrast to the conventional spray pumps, since the space arising on dispensing the product is filled by the evaporating easily volatilized organic solvent ingredient and air does not need to be conducted into the container. Even when the presence of an air opening because of the only very slight loss of the easily volatilized substances is acceptable, a pump without air opening is preferred.

An aerosol spray wax product is also part of the subject matter according to the invention. This aerosol spray wax product comprises a pressure resistant container with a spray head or a foam head and a sprayable or foamable composition contained in the pressure resistant container. This sprayable or foamable composition comprises (A) at least one wax or wax-like substance;
(B) at least one non-volatile, hydrophobic oil, which is a liquid at room temperature; and
(C) at least one hydrophobic liquified propellant.

Classical hair waxes are soluble or at least can be suspended in organic solvents. These solvents include easily volatilized alkanes, such as pentane and its isomers, which are liquid at normal pressures and at room temperature, as well as liquifiable propellant gases used in the aerosol, such as propane, butane and its isomers. If a hair wax composition is dissolved or suspended together with one of these propellant gases and filled in an aerosol container, it may be sprayed either as a fine spray or as spray foam like wax snow. A dense wax snow (frozen wax) is produced, when one uses a foam head instead of a spray head. The dense wax snow arises by heat loss due to evaporation of the propellant gas. The foam-like or flake-like consistency with the larger wax surface area permits very easy distribution on the hands and in the hair.

When the hair wax product according to the invention is an aerosol spray product according to the invention, the waxy composition has a preferably liquid sprayable or foamable consistency at room temperature (20° C.). The wax or wax-like substance (A) is preferably contained in the aerosol spray product according to the invention in an amount of from 5 to 30 percent by weight, especially preferably from 10 to 20 percent by weight. The liquid hydrophobic oil (B) is preferably contained in an amount of from 5 to 30 percent by weight, especially preferably from 10 to 20 percent by weight. The volatile hydrophobic substance (C) is present in an amount of preferably from 35 to 80 percent by weight, especially preferably 45 to 75 percent by weight. The non-volatile oils are partially replaced by easily volatilized, gaseous hydrophobic substances in contrast to the commercial hair wax products.

The easily volatilized hydrophobic substance (C) in the aerosol spray wax product according to the invention is preferably a liquid propellant gas, i.e. it is gaseous at room temperature under normal pressure conditions and liquifiable under pressure at room temperature. Suitable propellant gases include propane, n-butane, isobutane and fluorinated hydrocarbons, such as 1,1-difluoroethanes or 1,1,1,2-tetrafluoroethane or dimethyl ether. These propellant gases can be used alone or in a mixture, e.g. a mixture of propane and/or butane and dimethyl ether. A mixture of dimethyl ether and propane and/or butane is especially preferred. In addition to the propellant gas the easily volatilized hydrophobic substance (C) also includes a material that is liquid at room temperature which has a boiling point of from 30 to 100° C., preferably from 35 to 70° C. Liquid hydrocarbons, liquid cyclic or linear silicones (dimethylpolysiloxanes), or mixture of the foregoing materials, are especially suitable as the liquid hydrocarbons. Suitable hydrocarbons includes linear or branched alkanes with 5 to 7 carbon atoms, especially pentane. For example, hexamethyldisiloxane is especially suitable as a liquid easily volatilized silicone.

The pressure-tight aerosol container for the aerosol spray wax product according to the invention can be made from known materials for aerosol spray or foam products. Suitable materials include metals, such as aluminum or tin plate. Commercial spray heads and foam heads can be used for the aerosol containers for the aerosol spray wax product according to the invention.

Wax or Wax-like Substance (A)

Chiefly known waxes according to the state of the art can be used as the wax or wax-like substance (A) in the composition according to the invention. These waxes include animal, vegetable, mineral and synthetic waxes, solid paraffins, petrolatum (Vaseline®), ozocerite, montan wax, Fischer-Topsch waxes, polyolefin waxes, such as polybutene, bees wax, wool wax and its derivatives, such as wool wax alcohols, candela wax, caranuba wax, japan wax, hardened fats, fatty acid esters and fatty acid glycerides with solidification points above 40° C., polyethylene waxes and silicone waxes. The waxes or wax-like substances have a solidification point above 40° C., preferably above 55° C. The needle penetration number (0.1 mm, 100 g, 5 s, 25° C.; according to DIN 51 579) is preferably in a range of 2 to 70, especially from 3 to 40. Preferably at least one wax is present in the composition of the invention, which has a needle penetration point which is less than 40, especially preferably less than 20. Caranuba wax and ceresine wax with a needle penetration point of less than 20 or their mixture is especially preferred.

Non-volatile Hydrophobic Oil

The non-volatile hydrophobic oil (B) has a melting point under 25° C. and a boiling point over 250° C., preferably over 300° C. Generally oils known to those skilled in the art can be used as the non-volatile hydrophobic oil (B) according to the invention. These oils include vegetable oils, animal oils, mineral oils, silicone oils or their mixtures. Suitable silicone oils include polydimethylsiloxanes, phenylated silicones, polyphenylmethylsiloxanes, phenyltrimethicones, poly($C_1$- to $C_{20}$-)alkylsiloxanes and alkylmethylsiloxanes. Furthermore the following compounds are also suitable: hydrocarbon oils, such as paraffin oils, isoparaffin oils, squalane, oils from fatty acids and polyoles, especially triglycerides. Suitable vegetable oils include e.g. sunflower seed oils, coconut oil, castor oil, lanolin oils, jojoba oil, corn oil and soy oil. Hydrocarbon oils, especially mineral oils (paraffinum liquidum), are especially preferred.

Additional Emulsifier

Preferred embodiments of the hair wax product of the invention include at least one emulsifier, in order to improve the washability of the composition from the hair. The emulsifiers are preferably contained in an amount of from 0.5 to 20 percent by weight, especially preferably from 3 to 15 percent by weight. Preferred emulsifiers are selected from the group of non-ionic surfactants. Suitable non-ionic surfactants include, e.g., addition products of 2 to 30 mol ethylene oxide with fatty alcohols having 8 to 22 carbon atoms; addition products of 2 to 30 mol ethylene oxide with fatty acids containing 12 to 22 carbon atoms; addition products of 2 to 30 mol ethylene oxide with alkylphenols containing 8 to 15 carbon atoms in the alkyl groups; addition products of 1 to 5 mol propylene oxide with fatty alcohols having 8 to 22 carbon atoms; addition products of 1 to 5 mol of propylene oxide with fatty acids containing 12 to 22 carbon atoms; addition products of 1 to 5 mol propylene oxide with alkylphenols containing 8 to 15 carbon atoms in the alkyl groups;

fatty acid mono- and diesters having 12 to 22 carbon atoms of addition products of 1 to 30 mol ethylene oxide with glycerol;

addition products of 5 to 60 mol of ethylene oxide with castor oil; and monoesters, diesters and triesters of phosphoric acid and addition products of 2 to 30 mol of ethylene oxide with fatty alcohols having 8 to 22 carbon atoms; or mixtures thereof.

In a particularly preferred embodiment the emulsifiers have a wax-like consistency and a liquifying point over 25° C.

Cosmetic Additive Ingredients

The hair wax product according to the invention can also contain standard cosmetic additive ingredients that are suitable for this type of composition in addition to the above-mentioned ingredients.

solvents, such as water or univalent or multivalent $C_1$- to $C_2$-alcohols, especially ethanol, propanol, glycerol or glycols, in an amount of up to 10 percent by weight, preferably from 0.1 to 8 percent by weight.

cosmetic dyestuffs in an amount of up to six percent by weight, preferably from 0.1 to 4 percent by weight, e.g. C.I. Pigment Red 4 (C.I. 12 085), C.I. Pigment Green (C.I. 74 260), and/or C.I. Vat Blue 4 (C.I. 69 800).

Pearlescent pigments in an amount of up 25 percent by weight, preferably 1 to 20 percent by weight, e.g. such as those with a titanium dioxide/mica base.

Perfume and fragrance materials in an amount of up to 2 percent by weight, preferably from 0.01 to 1 percent by weight;

preservative materials in an amount of up to 1 percent by weight, preferably 0.01 to 0.5 percent by weight, especially parahydroxybenzoic acid ester, benzoic acid, salicylic acid, sorbic acid, mandelic acid, polyhexamethylene biguanidine hydrochloride or isothiazoline dertivative compounds;

film-forming polymers, such as polyvinyl pyrrolidone or vinylpyrrolidone/vinyl acetate copolymer in an amount of up to 5 percent by weight, preferably from 0.1 to 4 percent by weight; and hair care materials, such as betaine, in an amount of up to 5 percent by weight; preferably from 0.01 to 4 percent by weight.

Preparation

The hair wax product according to the invention can be made by melting the ingredients together and mixing them, without the easily volatilized substance (C). Subsequently the mixture is cooled and the easily volatilized substance (C) is added and mixed shortly before it solidifies. The still flowing mass is filled in the desired container (cup or other container) prior to solidification.

The spray wax product according to the invention can be made by melting the ingredients together and mixing them, without the easily volatilized substance (C). Subsequently the mixture is cooled to room temperature. The mass is then dissolved or suspended in the volatile liquid substance (C). This solution or suspension is filled in the spray container. In the case of a non-aerosol product a spray pump is provided. In the case of an aerosol product the propellant gas is supplied to the container. The aerosol container is then either provided with a spray head for producing a wax spray or with a foam head for producing a wax snow.

The following examples should illustrate the subject matter of the invention in more detail.

EXAMPLES

Example 1

Hair Wax

| | |
|---|---|
| 25.0 g | Polyglycerin ® 1894 (Ceresin, Penetration hardness 10 to 16 at 25° C.) |
| 25.0 g | Isododecane |
| 20.0 g | Paraffinum liquidum |
| 15.0 g | Caranuba wax |
| 10.0 g | Triceteareth-4 phosphate |
| 4.0 g | PEG-40 Hydrogenated Castor Oil |
| 0.6 g | Perfume |
| 0.4 g | Polyparabene |

The ingredients of the composition are mixed with each other, melted at high temperature, filled into a plastic cup and allowed to cool.

Example 2

Spray Wax Without Propellant

| | |
|---|---|
| 19.0 g | Paraffinum liquidum |
| 15.0 g | Polyglycerin ® 1894 (Ceresin, Penetration hardness 10 to 16 at 25° C.) |
| 5.0 g | Caranuba wax |
| 5.0 g | Triceteareth-4 phosphate |
| 5.0 g | PEG-40 Hydrogenated Castor Oil |
| 0.6 g | Perfume |
| 0.4 g | Polyparabene |
| 50.0 g | Pentane |

The ingredients of the composition are mixed with each other in the usual manner, filled in a container for non-aerosol spray products and provided with a commercially available mechanical spray pump.

Example 3

Aerosol Wax

| | |
|---|---|
| 13.0 g | Paraffinum liquidum |
| 10.5 g | Polyglycerin ® 1894 (Ceresin, Penetration hardness 10 to 16 at 25° C.) |
| 3.5 g | Caranuba wax |
| 3.5 g | Triceteareth-4 phosphate |
| 3.5 g | PEG-40 Hydrogenated Castor Oil |
| 0.6 g | Perfume |
| 0.4 g | Polyparabene |
| 35.0 g | Pentane |
| 24.0 g | Butane |
| 5.1 g | Isobutane |
| 0.9 g | Propane | a) The ingredients of the composition are filled into an aerosol can and provided with a commercial spray head. A finely divided wax spray of sufficient surface area is obtained when the product is dispensed from the aerosol container.

b) The ingredients of the composition are filled into an aerosol can and provided with a commercial spray head. A compact wax spray of sufficient surface area is obtained when the product is dispensed from the aerosol container.

The disclosure in German Patent Application 100 49 147.2-71 of Oct. 4, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in hair wax products containing waxes, non-volatile oils and volatile hydrophobic materials, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair wax product containing a sprayable or foamable wax like composition, wherein said wax-like composition comprises:

up to 10 percent by weight of water;

from 5 to 60% by weight of at least one wax or wax-like substance;

from 5 to 35% by weight of at least one non-volatile, liquid, hydrophobic oil having a melting point below 25° C. and a boiling point above 250° C.; and from 10 to 80% by weight of at least one easily volatilized, hydrophobic substance that is liquid or gaseous at room temperature and that has a boiling point of not more than 250° C.

2. The hair wax product as defined in claim 1, wherein said wax-like composition has a needle penetration number of not less than 10 at 25° C.

3. The hair wax product as defined in claim 1, wherein said at least one easily volatilized, hydrophobic substance is selected from the group consisting of volatile silicone compounds, hydrocarbons having from five to fourteen carbon atoms, volatile liquid paraffins and volatile liquid isoparaffins.

4. The hair wax product as defined in claim 1, wherein said wax-like composition comprises from 3 to 20 percent by weight of an emulsifier.

5. The hair wax product as defined in claim 4, wherein said emulsifier is selected from the group consisting of addition products of 2 to 30 mol ethylene oxide with fatty alcohols having 8 to 22 carbon atoms;
   addition products of 2 to 30 mol ethylene oxide with fatty acids containing 12 to 22 carbon atoms;
   addition products of 2 to 30 mol ethylene oxide with alkylphenols containing 8 to 15 carbon atoms in the alkyl groups;
   addition products of 1 to 5 mol propylene oxide with fatty alcohols having 8 to 22 carbon atoms;
   addition products of 1 to 5 mol of propylene oxide with fatty acids containing 12 to 22 carbon atoms;
   addition products of 1 to 5 mol propylene oxide with alkylphenols containing 8 to 15 carbon atoms in the alkyl groups;
   fatty acid mono- and diesters having 12 to 22 carbon atoms of addition products of 1 to 30 mol ethylene oxide with glycerol;
   addition products of 5 to 60 mol of ethylene oxide with castor oil;
   monoesters, diesters and triesters of phosphoric acid and addition products of 2 to 30 mol of ethylene oxide with fatty alcohols having 8 to 22 carbon atoms; or
   mixtures thereof.

6. The hair wax product as defined in claim 1, further comprising a container for the wax-like composition, said container having a mechanical pumping device and with a spray head or foam head and wherein said sprayable or foamable composition is contained in the container.

7. The hair wax product as defined in claim 6, wherein said at least one easily volatilized, hydrophobic substance is selected from the group consisting of volatile silicone compounds, hydrocarbons having from five to fourteen carbon atoms, volatile liquid paraffins and volatile liquid isoparaffins.

8. The hair wax product as defined in claim 6, wherein said composition comprises from 3 to 20 percent by weight of an emulsifier.

9. The hair wax product as defined in claim 8, wherein said emulsifier is selected from the group consisting of addition products of 2 to 30 mol ethylene oxide with fatty alcohols having 8 to 22 carbon atoms;
   addition products of 2 to 30 mol ethylene oxide with fatty acids containing 12 to 22 carbon atoms;
   addition products of 2 to 30 mol ethylene oxide with alkylphenols containing 8 to 15 carbon atoms in the alkyl groups;
   addition products of 1 to 5 mol propylene oxide with fatty alcohols having 8 to 22 carbon atoms;
   addition products of 1 to 5 mol of propylene oxide with fatty acids containing 12 to 22 carbon atoms;
   addition products of 1 to 5 mol propylene oxide with alkylphenols containing 8 to 15 carbon atoms in the alkyl groups; fatty acid mono- and diesters having 12 to 22 carbon atoms of addition products of 1 to 30 mol ethylene oxide with glycerol; addition products of 5 to 50 mol of ethylene oxide with castor oil;
   monoesters, diesters and triesters of phosphoric acid and addition products of 2 to 30 mol of ethylene oxide with fatty alcohols having 8 to 22 carbon atoms; or
   mixtures thereof.

10. The hair wax product as defined in claim 1, further comprising a pressure resistant container with a spray head or a foam head and wherein said sprayable or foamable composition is contained in the pressure resistant container, and contains from 35 to 80% by weight of said at least one easily volatilized, hydrophobic substance and said at least one easily volatilized, hydrophobic substance is a liquified propellant selected from the group consisting of propane, n-butane, isobutane and fluorinated hydrocarbons.

11. The hair wax product as defined in claim 10, wherein said at least one wax or wax-like substance is selected from materials which have a needle penetration number of less than 40 at 25° C.

12. The hair wax product as defined in claim 10, wherein said at least one non-volatile, liquid hydrophobic oil is selected from the group consisting of mineral oils, paraffin oils, isoparaffins and hydrocarbons.

13. The hair wax product as defined in claim 10, wherein said composition comprises from 3 to 20 percent by weight of an emulsifier.

14. The hair wax product as defined in claim 13, wherein said emulsifier is selected from the group consisting of addition products of 2 to 30 mol ethylene oxide with fatty alcohols having 8 to 22 carbon atoms;
   addition products of 2 to 30 mol ethylene oxide with fatty acids containing 12 to 22 carbon atoms;
   addition products of 2 to 30 mol ethylene oxide with alkylphenols
   containing 8 to 15 carbon atoms in the alkyl groups;
   addition products of 1 to 5 mol propylene oxide with fatty alcohols having 8 to 22 carbon atoms;
   addition products of 1 to 5 mol of propylene oxide with fatty acids containing 12 to 22 carbon atoms;
   addition products of 1 to 5 mol propylene oxide with alkylphenols
   containing 8 to 15 carbon atoms in the alkyl groups;
   fatty acid mono- and diesters having 12 to 22 carbon atoms of addition products of 1 to 30 mol ethylene oxide with glycerol;
   addition products of 5 to 60 mol of ethylene oxide with castor oil;
   monoesters, diesters and triesters of phosphoric acid and addition products of 2 to 30 mol of ethylene oxide with fatty alcohols having 8 to 22 carbon atoms; or
   mixtures thereof.

15. The hair wax product as defined in claim 1, wherein said wax-like composition contains from 20 to 60% by weight of said at least one wax or wax-like substance;
   from 10 to 35% by weight of said at least one non-volatile, liquid, hydrophobic oil; and
   from 10 to 35% by weight of said at least one easily volatilized, hydrophobic substance; and
   wherein said at least one easily volatilized hydrophobic substance is selected from the group consisting of liquid volatile silicones, hydrocarbons with from 5 to 14 carbon atoms, liquid volatile paraffins and liquid volatile isoparaffins; and
   wherein said wax-like composition has a needle penetration number of at least 10 at 25° C.

16. The hair wax product as defined in claim 15, wherein said wax-like composition contains from 3 to 20 percent by weight of an emulsifier.

17. The hair wax product as defined in claim 16, wherein said emulsifier is selected from the group consisting of addition products of 2 to 30 mol ethylene oxide with fatty alcohols having 8 to 22 carbon atoms;
- addition products of 2 to 30 mol ethylene oxide with fatty acids containing 12 to 22 carbon atoms;
- addition products of 2 to 30 mol ethylene oxide with alkylphenols
- containing 8 to 15 carbon atoms in the alkyl groups; addition products of 1 to 5 mol propylene oxide with fatty alcohols having 8 to 22 carbon atoms;
- addition products of 1 to 5 mol of propylene oxide with fatty acids containing 12 to 22 carbon atoms;
- addition products of 1 to 5 mol propylene oxide with alkylphenols containing 8 to 15 carbon atoms in the alkyl groups;
- fatty acid mono- and diesters having 12 to 22 carbon atoms of addition products of 1 to 30 mol ethylene oxide with glycerol;
- addition products of 5 to 60 mol of ethylene oxide with castor oil;
- monoesters, diesters and triesters of phosphoric acid and addition products of 2 to 30 mol of ethylene oxide with fatty alcohols having 8 to 22 carbon atoms; or
- mixtures thereof.

18. The hair wax product as defined in claim 6, wherein said wax-like composition contains from 10 to 30% by weight of said at least one wax or wax-like substance;
- from 10 to 30% by weight of said at least one non-volatile, liquid, hydrophobic oil; and
- from 20 to 70% by weight of said at least one easily volatilized, hydrophobic substance which is said liquid at room temperature and said liquid has a boiling point between 30 to 100° C.

19. The hair wax product as defined in claim 10, wherein said wax-like composition contains from 5 to 30% by weight of said at least one wax or wax-like substance and from 5 to 30% by weight of said at least one non-volatile, liquid, hydrophobic oil.

* * * * *